(12) United States Patent
Morimoto

(10) Patent No.: US 9,927,617 B2
(45) Date of Patent: Mar. 27, 2018

(54) HEAD-MOUNTED DISPLAY WHICH PROVIDES AN INDICATION OF AN ANGLE OF TILT THEREFOR RELATIVE TO A WEARER

(71) Applicant: Sony Corporation, Tokyo (JP)

(72) Inventor: Toshiyasu Morimoto, Kanagawa (JP)

(73) Assignee: Sony Corporation (JP)

( * ) Notice: Subject to any disclaimer, the term of this patent is extended or adjusted under 35 U.S.C. 154(b) by 0 days.

(21) Appl. No.: 14/383,697

(22) PCT Filed: Mar. 12, 2013

(86) PCT No.: PCT/JP2013/001584
§ 371 (c)(1),
(2) Date: Sep. 8, 2014

(87) PCT Pub. No.: WO2013/140744
PCT Pub. Date: Sep. 26, 2013

(65) Prior Publication Data
US 2015/0015461 A1    Jan. 15, 2015

(30) Foreign Application Priority Data

Mar. 22, 2012  (JP) ................................ 2012-065603

(51) Int. Cl.
*G02B 27/01* (2006.01)
*A61B 1/00* (2006.01)
*A61B 5/00* (2006.01)

(52) U.S. Cl.
CPC ...... *G02B 27/0176* (2013.01); *A61B 1/00048* (2013.01); *A61B 5/742* (2013.01); *G02B 27/017* (2013.01); *G02B 2027/0178* (2013.01); *G02B 2027/0187* (2013.01)

(58) Field of Classification Search
CPC .... A61B 5/742; G06F 3/013; G06K 9/00597; G02B 27/0176; G02B 2027/0178
USPC ............................................................ 345/8
See application file for complete search history.

(56) References Cited

U.S. PATENT DOCUMENTS

| 5,926,318 A * | 7/1999 | Hebert ........................... 359/618 |
| 5,991,085 A * | 11/1999 | Rallison et al. ............... 359/630 |
| 2009/0034820 A1 | 2/2009 | Sugiyama |
| 2012/0013984 A1 | 1/2012 | Ikeda |
| 2012/0235883 A1* | 9/2012 | Border ............... G02B 27/0093 345/8 |

FOREIGN PATENT DOCUMENTS

| JP | H1084518 A | 3/1998 |
| JP | 2001104331 A | 4/2001 |

(Continued)

OTHER PUBLICATIONS

International Search Report from International Publication PCT/JP2013/001584 dated May 24, 2013.

(Continued)

*Primary Examiner* — Gustavo Polo
(74) *Attorney, Agent, or Firm* — Lerner, David, Littenberg, Krumholz & Mentlik, LLP

(57) ABSTRACT

According to an illustrative embodiment, a head-mounted display is provided. The head-mounted display includes a detector for detecting an angle of tilt of the head-mounted display; and an output unit for outputting an indication of the angle of tilt.

20 Claims, 9 Drawing Sheets

(56) References Cited

FOREIGN PATENT DOCUMENTS

| JP | 2002515127 A | 5/2002 |
|----|--------------|--------|
| JP | 2004219664 A | 8/2004 |
| JP | 2008278972 A | 11/2008 |
| JP | 2011066393 A | 3/2011 |
| JP | 2011-145488 A | 7/2011 |
| JP | 2012023495 A | 2/2012 |
| WO | 2011118074 A1 | 9/2011 |

OTHER PUBLICATIONS

Chinese Office Action for Application No. 201380014431.7, dated Feb. 4, 2016.
Japanese Office Action for Application No. 2012065603, dated Feb. 16, 2016.

* cited by examiner

HEAD-MOUNTED DISPLAY WHICH PROVIDES AN INDICATION OF AN ANGLE OF TILT THEREFOR RELATIVE TO A WEARER

CROSS-REFERENCE TO RELATED APPLICATION

The present application is a national phase entry under 35 U.S.C. § 371 of International Application No. PCT/JP2013/001584 filed Mar. 12, 2013, published on Sep. 26, 2013 as WO 2013/140744 A1, which claims priority from Japanese Patent Application No. JP 2012-065603, filed in the Japanese Patent Office on Mar. 22, 2012.

TECHNICAL FIELD

The present technology relates to a head-mounted display that can be used for medical purposes.

BACKGROUND ART

A head-mounted display (HMD) that the user puts on the head for, for example, viewing images is known. For example, as one of the HMDs, there is known an HMD including image display surfaces and display elements for right and left eyes (see, PTL 1). The HMD having such a configuration can display images having a parallax to the left and right eyes of the user through the left and right display surfaces, and hence can present three-dimensional (3D) images without crosstalk.

Meanwhile, also in an endoscope apparatus and the like used for medical purposes, a practical use of a 3D endoscope apparatus that can present 3D images is in consideration. An endoscopic surgery is less invasive for patients than a general surgical operation, and hence is popular in recent years. However, an affected part(s) is checked only by images during a surgery, and hence it is sometimes difficult to perceive a depth with traditional two-dimensional (2D) images. Therefore, it is expected that connecting and using the HMD capable of providing 3D images to a 3D endoscope apparatus can realize a more correct and rapid endoscopic surgery while viewing realistic images of the affected part.

CITATION LIST

Patent Literature

[PTL 1]
Japanese Patent Application Laid-open No. 2011-145488

SUMMARY OF INVENTION

For wearing the HMD having the above-mentioned configuration, it is typically necessary for the user to adjust an HMD mounting position to be such a position that a blurred image and an out-of-focus image are not generated, that is, a position in which the display surfaces and the left and right eyes are opposed to each other while viewing images displayed on the display surfaces.

However, a doctor (user) is not allowed to touch the HMD from a hygiene viewpoint upon wearing of the HMD during a surgery, and hence the user cannot adjust the mounting position by himself or herself. Therefore, a person other than the user needs to help the user wear the HMD. However, in this case, it is difficult for such a person to check position relationships between the eyes of the user and the display surfaces, which makes adjustment of a relative position of the HMD to the user difficult.

In view of the above-mentioned circumstances, there is a need for providing an HMD that allows adjustment of a relative position thereof to a user without checking displayed images.

As described above, according to the embodiments of the present technology, it is possible to provide an HMD that allows adjustment of a relative position thereof to a user without checking displayed images.

According to an illustrative embodiment, a head-mounted display includes a detector for detecting an angle of tilt of the head-mounted display; and an output unit for outputting an indication of the angle of tilt.

DESCRIPTION OF EMBODIMENTS

Hereinafter, embodiments according to the present technology will be described with reference to the drawings.

First Embodiment

Figure 1:
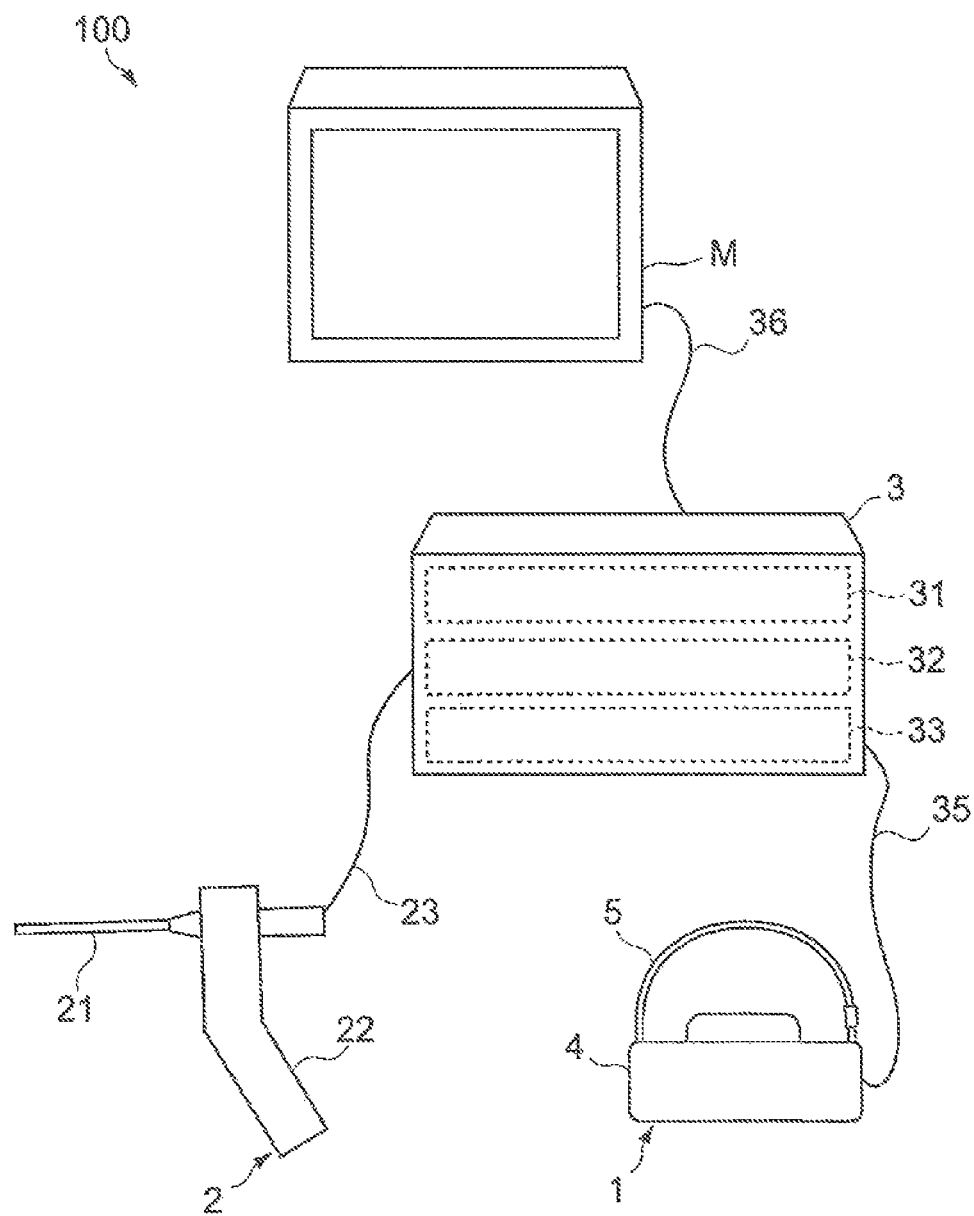
FIG. 1 is a view schematically showing a configuration example of an endoscopic system according to a first embodiment of the present technology.

[Endoscopic System]
FIG. 1 is a view schematically showing a configuration example of an endoscopic system according to an embodiment of the present technology. An endoscopic system 100 according to this embodiment includes a head-mounted display (HMD) 1, an endoscope apparatus 2, and a processor unit 3. The endoscopic system 100 according to this embodiment is used in the following manner. Specifically, during an endoscopic surgery, a doctor (user) wearing the HMD 1 inserts the endoscope apparatus 2 into the body of a patient and performs treatments such as resection on an affected part(s) while checking through the HMD 1 a state of the affected part that is imaged by the endoscope apparatus 2.

The endoscope apparatus 2 includes, for example, an insertion portion 21 and an operation portion 22. The insertion portion 21 has a tubular shape that can be inserted into a body. The insertion portion 21 includes therein an image sensor such as a CMOS (complementary metal-oxide semiconductor) image sensor and an optical system such as a lens for imaging an affected part(s), which are not shown in the figure. Further, in this embodiment, two image sensors, two optical systems, and the like are provided for capturing right eye and left eye images having a parallax. With this, 3D image data for stereoscopically displaying the affected part can be acquired.

In addition, for example, a knife or forceps for resecting or holding the affected part is/are inserted into the insertion portion 21. The operation portion 22 is configured to perform an operation on the insertion portion 21 and the like while gripped by a surgery assistant or the like. Further, the operation portion 22 is connected to the processor unit 3 via a cable 23.

The processor unit 3 includes, for example, an image processing unit 31, a light source 32, and a converter 33. For example, the image processing unit 31 serves to process images acquired by the endoscope apparatus 2. The light source 32 serves to irradiate the affected part with light upon imaging by the endoscope apparatus 2. The converter 33 serves to perform conversion processing on signals relating to images to be outputted to the HMD 1. The light emitted from the light source 32 is guided to a distal end of the insertion portion 21 via, for example, light guide fibers provided inside the insertion portion 21.

Further, in the image processing unit 31, the right eye and left eye images captured can be overlapped and processed as the 3D image data. The 3D image data is outputted to a monitor apparatus M via, for example, a cable 36, which allows a helper and the like other than the user wearing the HMD 1 to also check the affected part during the surgery.

The HMD 1 is electrically connected to the processor unit 3 and worn by the user who makes instructions to the surgery assistant or the like who operates the endoscope apparatus 2 while the user is observing endoscopic images. The connection method for the HMD 1 and the processor unit 3 is not particularly limited and a wired connection or a wireless connection may be used. In this embodiment, for example, the wired connection is used. Specifically, the HMD 1 and the processor unit 3 are connected to each other via a cable 35 outputted and inputted from/to HDMI (high-definition multimedia interface) terminals.

The signals relating to the right eye and left eye images captured by the endoscope apparatus 2 are processed as image signals by the image processing unit 31. After that, the image signals are each processed by the converter 33 as image data adapted for the HMD 1, and outputted to the HMD 1 via the cable 35. Note that, the processor unit 3 may be configured to supply the HMD 1 with a driving electrical power via the cable 35.

Note that, the converter 33 that processes output signals to the HMD 1 is not limited to the example shown in the figure in which the converter 33 is housed in a single casing together with the image processing unit 31 and the like. The converter 33 may be housed in a separate casing other than that for the image processing unit 31 and the like.

Next, a detailed configuration of the HMD 1 according to this embodiment will be described.

[HMD]

Figure 2:
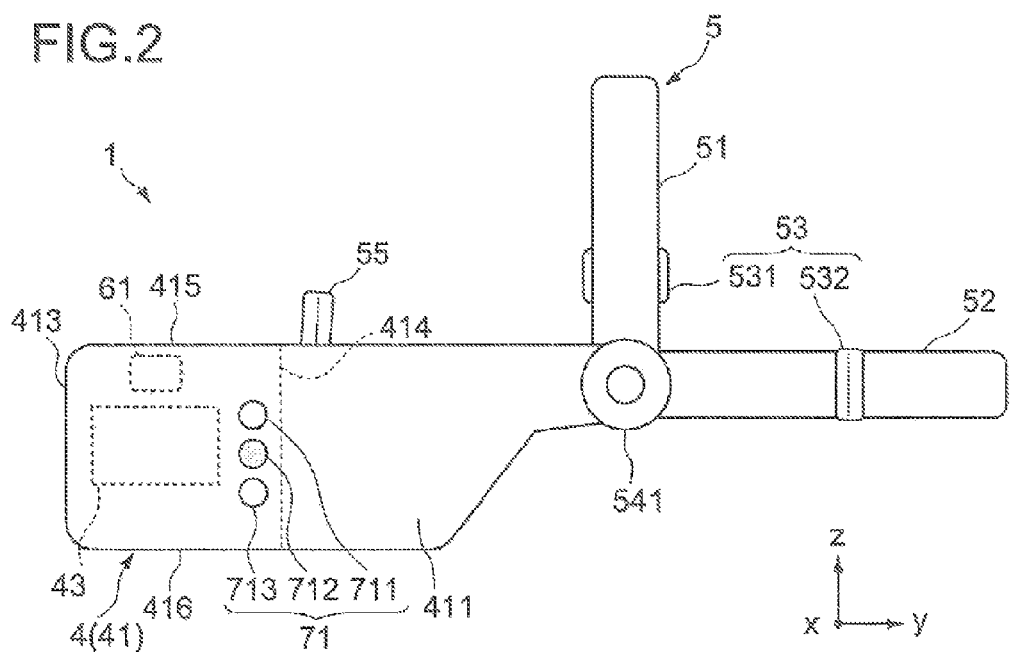
FIG. 2 is a schematic side view showing a head-mounted display according to the first embodiment of the present technology.
Figure 3:
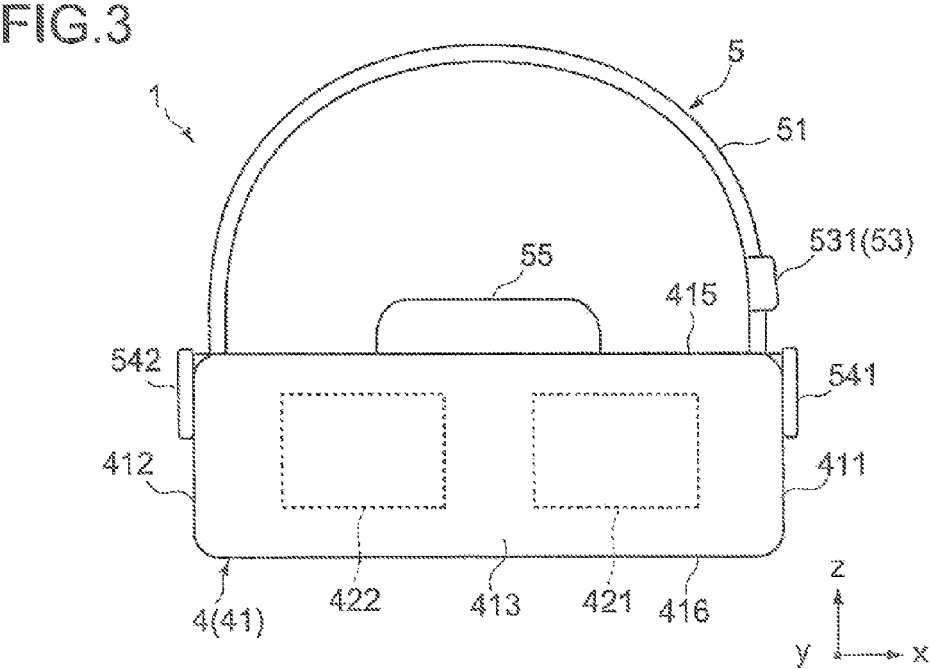
FIG. 3 is a schematic front view showing the head-mounted display according to the first embodiment of the present technology.
Figure 4:
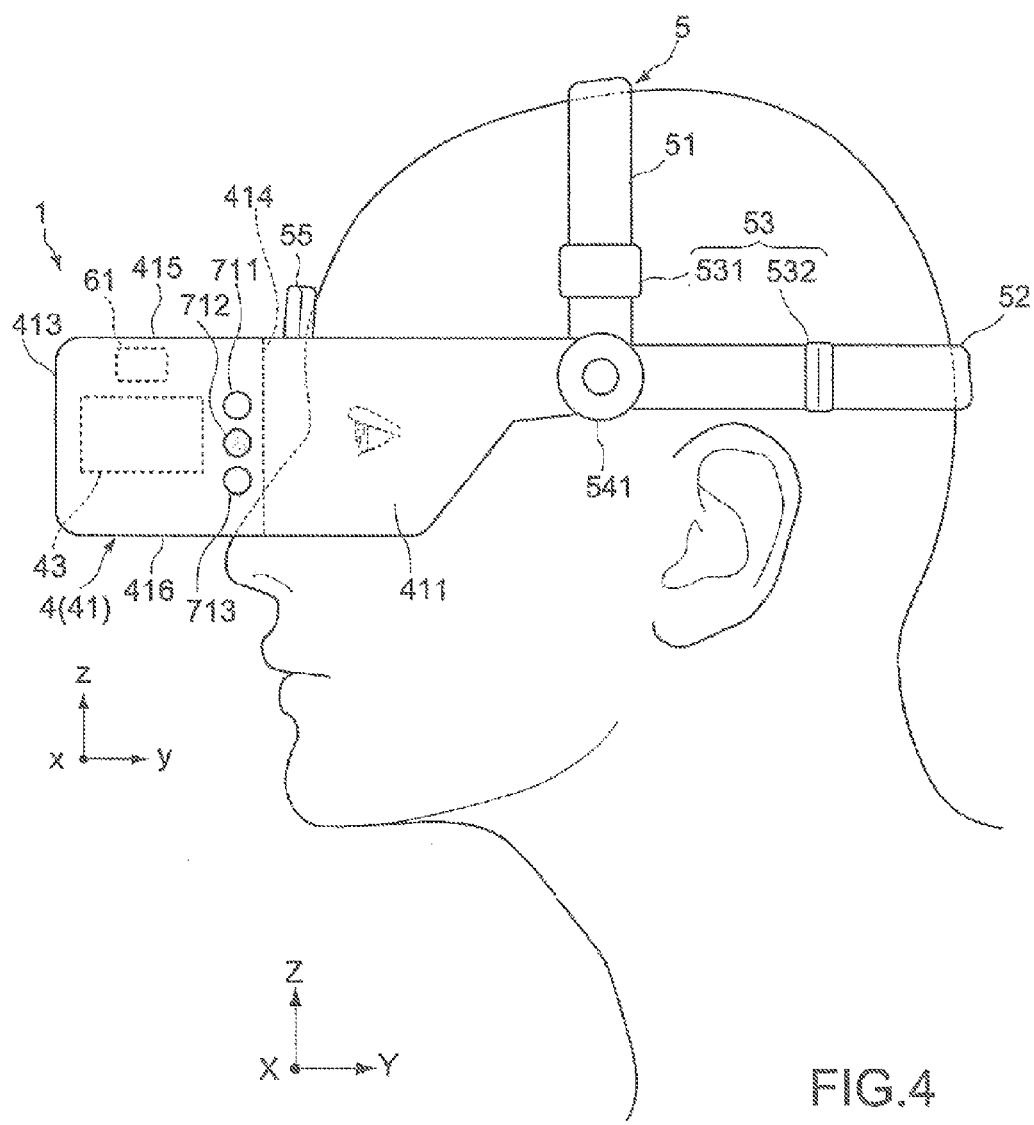
FIG. 4 is a schematic side view showing a state in which a user wears the head-mounted display according to the first embodiment of the present technology.
Figure 5:
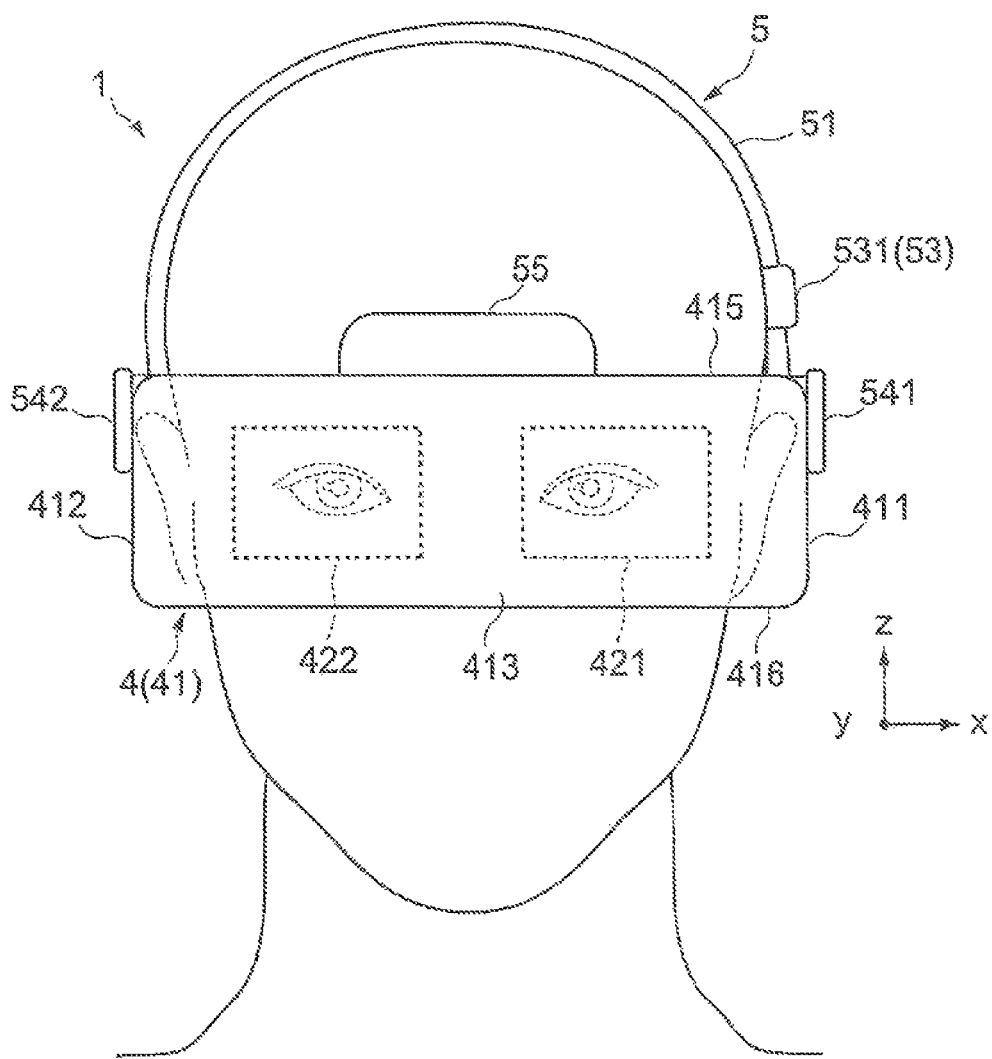
FIG. 5 is a schematic front view showing the state in which the user wears the head-mounted display according to the first embodiment of the present technology.
Figure 6:
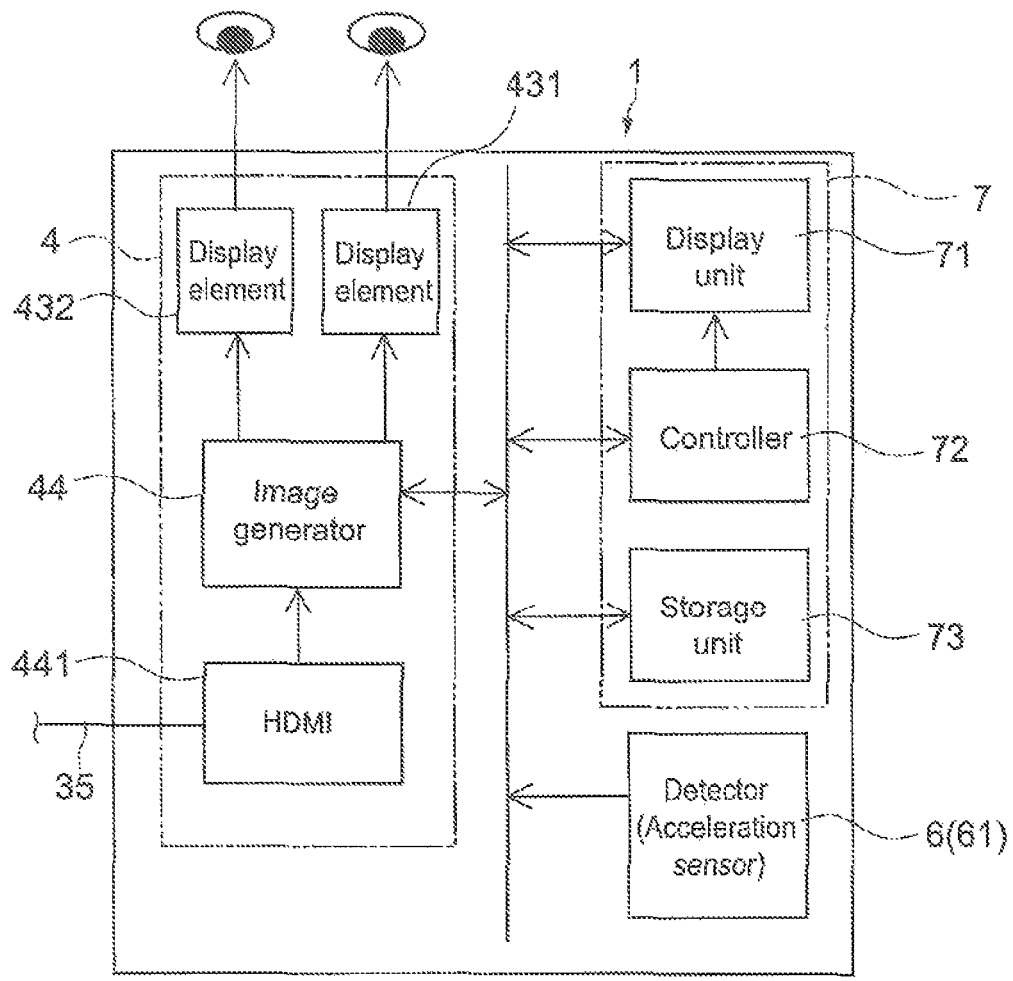
FIG. 6 is a block diagram showing an apparatus configuration of the head-mounted display according to the first embodiment of the present technology.

FIGS. 2 to 6 are views each showing the configuration of the HMD 1 according to this embodiment. FIG. 2 is a schematic side view. FIG. 3 is a schematic front view. FIG. 4 is a schematic side view showing a state in which the user wears the HMD 1. FIG. 5 is a schematic front view showing the state in which the user wears the HMD 1. FIG. 6 is a block diagram showing an apparatus configuration. The HMD 1 includes a main body 4, a mounting portion 5, a detector 6, and an output unit 7.

Note that, an x-axis direction and a y-axis direction in the figures each indicate a horizontal direction in an xyz coordinate system to which the HMD 1 belongs. The x-axis direction (first axis direction) corresponds to left and right directions of the main body 4. The y-axis direction (second axis direction) corresponds to front and rear directions of the main body 4, which are orthogonal to the x-axis direction. A z-axis direction indicates a direction orthogonal to the x-axis direction and the y-axis direction and corresponds to upper and lower directions of the main body 4.

Further, an X-axis direction and a Y-axis direction in the figures each indicate a horizontal direction in an XYZ coordinate system to which the user belongs, and an XY plane indicates a "horizontal plane." That is, the X-axis direction indicates left and right directions as viewed from the user and the Y-axis direction is orthogonal to the X-axis direction and indicates front and rear directions as viewed from the user (front and back directions of the user). A Z-axis direction is orthogonal to the X-axis direction and the Y-axis direction and indicates a vertical direction.

The HMD 1 according to this embodiment is formed of, for example, a goggle-shaped non-see-through HMD. Further, the main body 4 is provided with the mounting portion 5, which will be described later. When the mounting portion 5 is mounted on the head of the user, the main body 4 is located in front of the left and right eyes of the user.

Hereinafter, configurations of the respective components will be described.

(Main Body)

The main body 4 includes a casing 41, a first display surface (display surface) 421 for a left eye, a second display surface (display surface) 422 for a right eye, a left-eye display element 431, a right-eye display element 432, and an image generator 44.

The main body 4 is configured as an image display apparatus that presents a predetermined image captured by the endoscope apparatus 2 to the user. Specifically, the image generator 44 first generates, based on image data acquired via the processor unit 3, image signals to be outputted to the left and right display elements 431 and 432, respectively. Then, the display elements 431 and 432 emit image light beams corresponding to those image signals to the display surfaces 421 and 422, respectively, so that images are presented to the user.

The casing 41 is, as a whole, configured to fit the face, covering the left and right eyes of the user. The casing 41 includes a left side surface (first side surface) 411 and a right side surface (second side surface) 412 that are opposed to each other in the x-axis direction, a front surface 413 and an eye-side surface 414 that are opposed to each other in the y-axis direction, and an upper surface 415 and a lower surface 416 that are opposed to each other in the z-axis direction.

The eye-side surface 414 is configured to be opposed to the left and right eyes of the user in front of and in proximity to the left and right eyes. For example, in the center of the eye-side surface 414, a cutout may be formed corresponding to the nose shape of the user. Meanwhile, the front surface 413 is provided in front of the user wearing the HMD 1 and is formed to have a rectangular shape, for example. The left side surface 411 and the right side surface 412 may be located on the left- and right-hand sides of the face of the user, respectively, upon mounting. For example, the left side surface 411 and the right side surface 412 may be configured to cover up to (the vicinities of) the left and right temples of the user. Upon mounting, the thus configured casing 41 can almost completely cover the eyes of the user. Thus, light from the outside is not incident upon the eyes of the user, which makes it easier for the user to view images.

The casing 41 houses the display elements 431 and 432, the image generator 44, and the like. Note that, the casing 41 is not limited to the above-mentioned configuration. For example, a configuration in which the left and right side surfaces 411 and 412, the front surface 413, the upper surface 415, and the lower surface 416 except for the eye-side surface 414 are smoothly coupled to one another to form a single outer surface may be used.

In the eye-side surface 414, the display surfaces 421 and 422 are arranged along the x-axis direction. The display surfaces 421 and 422 are arranged to be orthogonal to the y-axis direction so that optical axe of the outputted image light beams are parallel to the y-axis direction.

The display surfaces 421 and 422 are configured to be capable of displaying the right eye and left eye images, which have been captured by the endoscope apparatus 2 and subjected to predetermined processing, to the left eye and the right eye of the user, respectively. The shape and size of the display surfaces 421 and 422 are not particularly limited. In this embodiment, each of the display surfaces 421 and 422 has a rectangular shape with about 16 mm in the vertical direction and about 30 mm in the horizontal direction. The material of the display surfaces 421 and 422 is not particularly limited as long as it has a see-through property. For example, a plastic plate, a glass plate, or the like is used as the material of the display surfaces 421 and 422.

In this embodiment, the image generator 44 includes an image data conversion circuit or the like that converts the right eye and left eye image data sent from the processor unit 3 into the image signals for the HMD 1. The image generator 44 acquires endoscopic image data from an HDMI input terminal 441 connected to the cable 35.

In addition, the image generator 44 may perform predetermined offset processing or the like on the image data to generate left-eye and right-eye image signals suitable for the HMD 1. With this, it is possible to present a desired 3D image to the user. The amount of offset in the offset processing is calculated based on, for example, distances between eyes and the display elements 431 and 432 of the HMD 1, a distance between both eyes, or a virtual image position, which will be described later.

The image generator 44 outputs the generated left-eye and right-eye image data to the left and right display elements 431 and 432, respectively.

The left and right display elements 431 and 432 output, based on the image data inputted from the image generator 44, the image light beams to the left and right display surfaces 421 and 422. The display elements 431 and 432 are arranged to be respectively opposed to the display surfaces 421 and 422 in the y-axis direction, for example. With this, the optical axes of the image light beams, which are out- putted from the display elements 431 and 432 and the display surfaces 421 and 422, become parallel to the y-axis direction.

In this embodiment, the display elements 431 and 432 are formed of organic EL (electroluminescence) elements. The use of the organic EL elements as the display elements 431 and 432 can achieve downsizing, high contrast, a rapid response, and the like.

As the display elements 431 and 432, for example, a plurality of red organic EL elements, green organic EL elements, blue organic EL elements, and the like are arranged in a matrix form. By being driven by a driving circuit of active matrix type, simple (passive) matrix type, or the like, these elements emit light by themselves at a predetermined timing with a predetermined luminance and the like. Further, the display elements 431 and 432 are configured to display a predetermined image by the driving circuit being controlled according to the image signals generated by the image generator 44.

Note that, the display elements 431 and 432 are not limited to the above-mentioned configuration. For example, a liquid crystal display (LCD) and the like may be used.

Between the display elements 431 and 432 and the display surfaces 421 and 422, for example, a plurality of eye lenses (not shown) are provided as optical systems. By causing these eye lenses and the eyes of the user to be opposed to each other with a predetermined distance therebetween, it is possible for the user to observe a virtual image as if the virtual image is displayed at a predetermined position (virtual image position). The virtual image position and the size of the virtual image are set depending on the configurations of the display elements 431 and 432 and the optical systems and the like. For example, the size of the virtual image is 750 inches adapted for a movie size and the virtual image position is set to be located at a position away from the user by about 20 m.

Here, in order to allow the user to observe the virtual image, the main body 4 is positioned with respect to the user so that the image light beams outputted from the display elements 431 and 432, with the y-axis direction being an optical direction thereof, form images respectively on the irises of the left and right eyes through the eye lenses and the like.

Therefore, in order to allow the user to observe the predetermined image, it is necessary to position the main body 4 so that the display surfaces 421 and 422 and the left and right eyes of the user are opposed to each other in the y-axis direction. In other words, the main body 4 is positioned so that the x-axis direction in which the display surfaces 421 and 422 are arranged becomes parallel to the horizontal plane (XY plane). Hereinafter, such a relative position of the main body 4 to the user is referred to as a "suitable relative position."

When the main body 4 is not located at the suitable relative position, an out-of-focus image or a blurred 3D image is generated and the user cannot view a desired image. Therefore, upon the mounting of the HMD 1, it is necessary to adjust the main body 4 to be located at the suitable relative position. Further, during the mounting, it is necessary to fix the main body 4 to the head to prevent this position from changing. In this embodiment, the relative position of the main body 4 is adjusted and fixed by the mounting portion 5, which will be described in the following.

(Mounting Portion)

The mounting portion 5 includes bands 51 and 52, an adjuster 53, left and right attachment members 541 and 542, and a forehead pad 55. The mounting portion 5 is provided to the main body 4 to be mountable on the head of the user so that the HMD 1 is located at the suitable relative position to the user, that is, the display surfaces 421 and 422 and the left and right eyes of the user are opposed to each other in the y-axis direction.

Referring to FIGS. 4 and 5, a schematic configuration of the mounting portion 5 according to this embodiment will be described. The bands 51 and 52 are attached via the main body 4 and the attachment members 541 and 542. The bands 51 and 52 each extend, for example, from the left side surface 411 of the casing 41 through the parietal region or the occipital region of the user to the right side surface 412. In addition, the adjuster 53 is configured to be capable of adjusting the length of the bands 51 and 52, and hence the relative position of the main body 4 to the user in a height direction and the front and rear directions can be adjusted. Further, the forehead pad 55 is configured to be able to abut against the forehead of the user. By adjusting the length of the band 52 passing through the occipital region, it is possible to fix the relative position in the front and rear directions of the user through the forehead pad 55 and the band 52.

The bands 51 and 52 both include, for example, two short bands to be attached to the attachment members 541 and 542. The bands 51 and 52 are configured to become a single band as a whole by these short bands being overlapped with each other by a predetermined length and fixed. The adjuster 53, which will be described later, is used for the fixing. Further, for the material of the bands 51 and 52, for example, a rubber, plastic, cloth, or the like is used in view of strength and flexibility thereof.

In this embodiment, the adjuster 53 adjusts the relative position of the main body 4 to the user. The adjuster 53 is attached to, for example, each of the bands 51 and 52 and includes adjustment members 531 and 532 capable of adjusting the length of the bands 51 and 52 from the attachment member 541 to the attachment member 542.

For each of the adjustment members 531 and 532, for example, a configuration of a buckle or a latch used for a belt or the like may be used. With this configuration, it is possible to arbitrarily fix and change the overlapping length of the respective two short bands of the bands 51 and 52, and the length of the bands 51 and 52 can be changed. The configurations of the adjustment members 531 and 532 are not particularly limited, and may be appropriately selected depending on the material, shape, and the like of the bands 51 and 52.

In this embodiment, the left and right attachment members 541 and 542 are provided to the left and right side surfaces 411 and 412, respectively. The configurations of the attachment members 541 and 542 are not particularly limited. For example, a swaging configuration in which the bands 51 and 52 are, at one ends thereof, overlapped with each other and attached to the main body 4 may be used. Further, the attachment members 541 and 542 may be configured so that the bands 51 and 52 are each rotatable with respect to the main body 4 within a predetermined angle range.

The forehead pad 55 is provided to protrude from the eye-side surface 414 of the main body 4 above the upper surface 415, for example. The configuration of the forehead pad 55 is not particularly limited and a cushion configuration is used for a surface to abut against the user in view of a wearing comfort of the user and the like. Further, if necessary, the angle with respect to the main body 4 and the height position of the forehead pad 55 in the z-axis direction may be configured to be adjustable. In addition, if necessary, the forehead pad 55 may be configured to be detachable.

(Detector)

The detector 6 is provided to the main body 4. The detector 6 detects a tilt of the main body 4 with respect to the horizontal plane (XY plane) and generates a signal relating to an angle of the tilt. The detector 6 includes an acceleration sensor 61 in this embodiment. The acceleration sensor 61 is provided in the left side surface 411 of the main body 4, for example.

The acceleration sensor 61 is, for example, a two-axis acceleration sensor that outputs electrical signals corresponding to acceleration of gravity in the x-axis direction and the z-axis direction. That is, the acceleration sensor 61 outputs, for example, a signal relating an angle of the tilt of the main body 4 with respect to the horizontal plane about a y-axis to a controller 72 of the output unit 7, which will be described later.

The acceleration sensor 61 may be a single-axis acceleration sensor that outputs a signal corresponding to acceleration of gravity in either one of the x-axis direction and the z-axis direction. Also with this, it is possible to output the signal relating to the angle of the tilt. Otherwise, a three-axis acceleration sensor may be used. In this case, it is possible to also detect an angle of the tilt of the main body 4 with respect to the horizontal plane about an x-axis in addition to the other angles. Further, depending on the apparatus configuration of the HMD 1, a piezoresistive type acceleration sensor, a capacitance type acceleration sensor, and other type acceleration sensors may be appropriately used.

(Output Unit)

The output unit 7 is provided to the main body 4 and outputs angle information regarding to the tilt of the main body 4 according to the signal of the detector 6. The output unit 7 includes, in this embodiment, a display unit 71, the controller 72, and a storage unit 73. Note that, in this embodiment, the controller 72 and the storage unit 73 are housed in the casing 41.

The controller 72 is typically formed of an MPU (microprocessing unit) or the like. The controller 72 performs predetermined arithmetic processing according to a program stored in the storage unit 73 and makes a predetermined determination based on the processing result. In addition, the determination result is outputted to the display unit 71.

The controller 72 first calculates, according to a signal outputted from the acceleration sensor 61, the angle of the tilt of the main body 4 with respect to the horizontal plane about the y-axis.

Here, when the angle of the tilt is 0, the x-axis direction of the main body and the horizontal plane are parallel to each other and thus the main body 4 is located at the suitable relative position. Further, when such an angle is smaller than a predetermined angle, it is accepted as a margin of error and it is considered that the main body 4 is located at the suitable relative position. Meanwhile, when such an angle is equal to or larger than the predetermined angle, it becomes difficult to view an image and it is not considered that the main body 4 is located at the suitable relative position. Thus, it is necessary to adjust the relative position.

Accordingly, based on a calculation result, the controller 72 determines whether the head-mounted display is in a first state in which the angle of the tilt is equal to or larger than a predetermined angle or a second state in which the angle of the tilt is smaller than the predetermined angle. The "predetermined angle of the tilt" is set to be a maximum angle of the tilt with respect to the horizontal plane, which is acceptable in observing the image by the user. That is, the first state represents a state in which it is not considered that the main body 4 is located at the suitable relative position because the main body 4 tilts with respect to the horizontal plane. Meanwhile, the second state represents a state in which it is considered that the main body 4 is located at the suitable relative position because the main body 4 is almost horizontal.

In addition, when determining that the head-mounted display is in the first state, the controller 72 further determines whether a direction of the tilt of the main body 4 with respect to the horizontal plane about the y-axis is a first direction (left tilt direction) or a second direction (right tilt direction) different from the left tilt direction. The determination result is outputted to a driving circuit of LEDs 711 to 713. Here, the "left tilt direction" means such a direction that a left-hand side of the main body 4 tilts downward in the vertical direction. Meanwhile, the "right tilt direction" means such a direction that a right-hand side of the main body 4 tilts downward in the vertical direction.

The storage unit 73 includes a RAM (random access memory), a ROM (read only memory), another semiconductor memory, and the like. The storage unit 73 stores a program and the like used for various arithmetic operations by the controller 72. For example, the ROM is formed of a non-volatile memory and stores a program and a setting value for causing the controller 72 to execute arithmetic processing such as calculation of the angle of the tilt. Further, the storage unit 73 is enabled by, for example, a non-volatile semiconductor memory to store a program and the like for determining whether the head-mounted display is in the first state, the second state, or the like. In addition, those programs stored in the semiconductor memory and the like in advance may be loaded into the RAM and executed by the controller 73.

In this embodiment, the display unit 71 includes the three LED lamps (LED) 711, 712, and 713 arranged on the left side surface 411 of the main body 4, and the driving circuit for causing any of the LEDs 711 to 713 to emit light based on an output from the controller 72. The display unit 71 is configured to output different angle information depending on the first state and the second state.

The LEDs 711 to 713 are arranged from the upper surface 415 side to the lower surface 416 side along the z-axis direction in the stated order. The driving circuit causes any one of the LEDs 711 to 713 to light up based on the determination result of the controller 72. Further, the LEDs 711 to 713 may emit different color light. For example, the LEDs 711 and 713 emit yellow light and the LED 712 in the center emits green light.

For example, when it is determined that the head-mounted display is in the first state and the tilt direction is the right tilt direction, the LED 711 is configured to emit yellow light, and, when it is determined that the head-mounted display is in the first state and the tilt direction is the left tilt direction, the LED 713 is configured to emit yellow light. Meanwhile, when it is determined that the head-mounted display is in the second state, that is, horizontal, the LED 712 is configured to emit green light.

Therefore, by checking the LED of the LEDs 711 to 713, which lights up, it is possible to check whether or not the main body 4 tilts with respect to the horizontal plane, and further the tilt direction. With this, even if the user cannot correct the tilt of the HMD 1 by himself or herself, the helper or the like can correct the tilt while checking the light of the LED.

Further, regarding the LEDs 711 to 713, for example, as viewed from the left-hand side of the user, the LED 711 on the upper surface 415 side in the right tilt direction that tilts upward in the vertical direction with respect to the horizontal plane lights up, and the LED 713 on the lower surface 416 side in the left tilt direction that tilts downward in the vertical direction. With this, it is possible to associate the arrangement of the LEDs 711 to 713 that light up with the tilt direction in an intuitive manner.

In addition, by using the LEDs for the display unit 71 according to this embodiment, the light colors thereof can be appropriately selected. For example, as in this embodiment, by using the green, yellow, and the like that suggest traffic light, more intuitive display can be realized.

Hereinafter, an example of a mounting method for the HMD 1 according to this embodiment will be described.

[Mounting Method Example]

Figure 7:
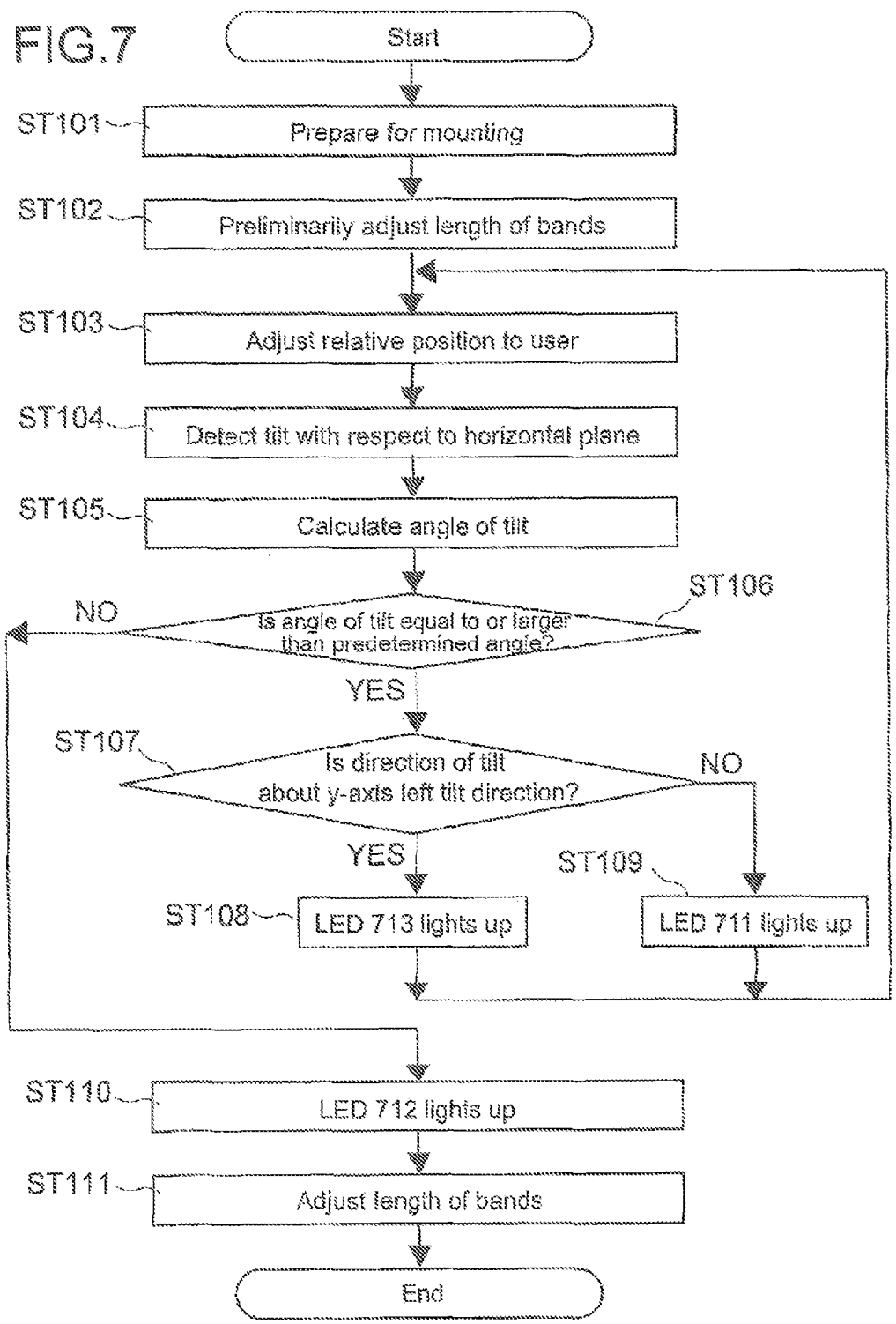
FIG. 7 is a flowchart showing an example of a mounting method for the head-mounted display according to the first embodiment of the present technology.

FIG. 7 is a flowchart showing an example of a mounting method for the HMD 1. Here, an example in which, in the case where a user who tries to perform an endoscopic surgery using the endoscope apparatus 2 has already performed hand antisepsis, and hence the user cannot adjust the relative position of the HMD 1 by himself or herself, a mounting helper (hereinafter, abbreviated as helper) near the user mounts the HMD 1 on the user will be described.

First, the HMD 1 is prepared by the helper adjusting the bands 51 and 52 to be longer than the length expected upon mounting (Step ST101). At this time, the HMD 1 may be activated in advance. Further, for example, the helper performs the preparation standing on the left-hand side of the user, if necessary, with a step in order to put the helper at a height to easily assist the mounting of the HMD 1.

Next, the helper mounts the HMD 1 on the head from above the user, and the length of the bands 51 and 52 is preliminarily adjusted via the adjustment members 531 and 532 (Step ST102). The bands 51 and 52 at this time are set to have an extra length so that the relative position of the HMD 1 to the user is not fixed and the relative position can be adjusted. Further, the band 51 is attached to the parietal region of the user and the band 52 is attached to the occipital region of the user.

In addition, the relative position of the HMD 1 to the user is adjusted (Step ST103). Specifically, the tilt of the main body 4 is adjusted so that the height of the display surfaces 411 and 412 of the HMD 1 substantially corresponds to the height of the left and right eyes of the user and the x-axis direction of the HMD 1 is almost parallel to the horizontal plane. At this time, the length of the band 51 may be adjusted by the adjustment member 531. Here, the bands 51 and 52 are adjusted to have an extra length, the adjustment of the relative position of the main body 4 can be easily performed.

Here, the helper mounts the HMD 1 from the left-hand side of the user. Therefore, it is relatively easy to grasp whether or not the y-axis direction of the main body 4 is parallel to the horizontal plane, but it is difficult to grasp whether or not the x-axis direction of the main body 4 is parallel to the horizontal plane. Therefore, even when the adjustment of the relative position of the main body 4 is performed, actually, the x-axis direction of the main body 4 may not be parallel to the horizontal plane and the main body 4 may tilt with respect to the horizontal plane about the y-axis. That is, the main body 4 may not be located at the suitable relative position.

Figure 8:
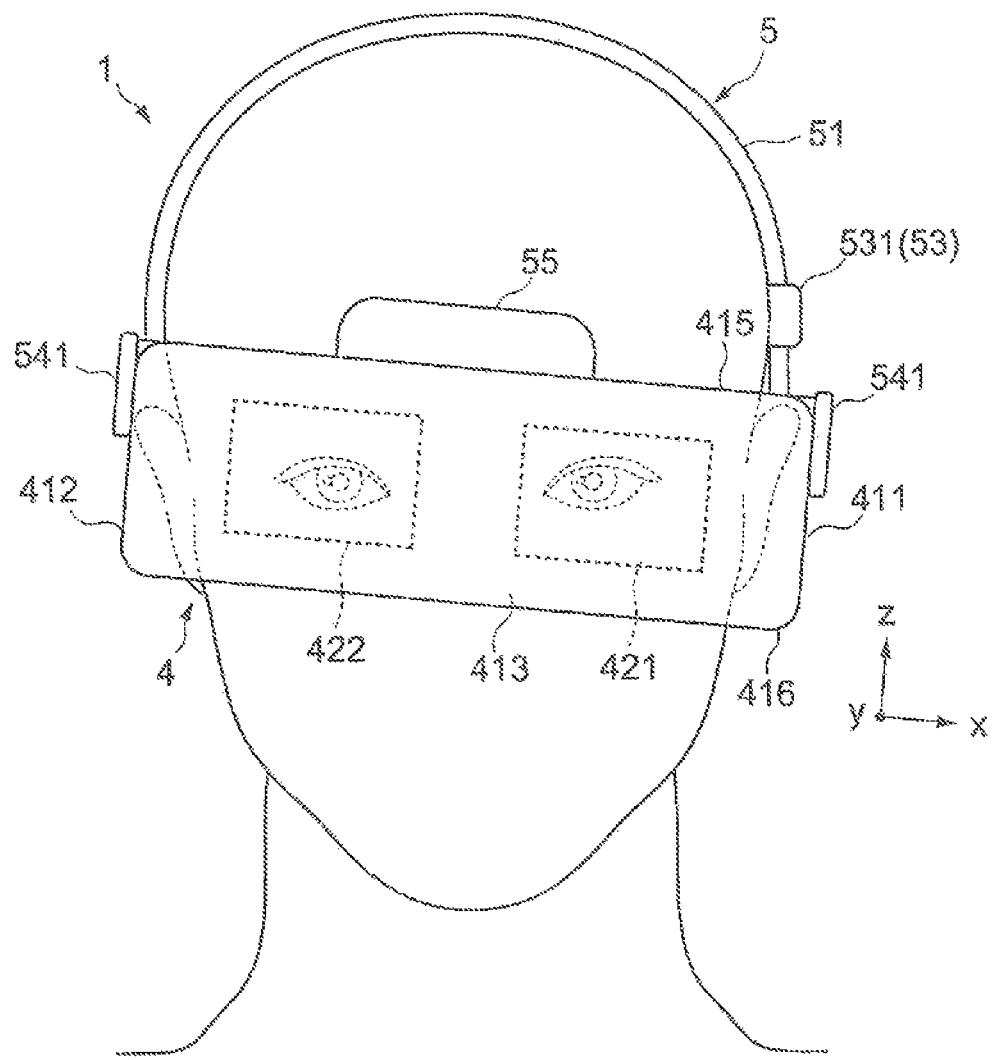
FIG. 8 is a schematic front view showing a state in which the user wears the head-mounted display according to the first embodiment of the present technology, specifically, a state in which the user wears the head-mounted display with a main body tilting with respect to a horizontal surface about a second axis.

FIG. 8 shows a state in which the HMD 1 is mounted on the user with the main body 4 tilting with respect to the horizontal plane about the y-axis. In this case, the x-axis direction is not parallel to the horizontal plane and the height of the left and right eyes of the user does not correspond to the height of the display surfaces 411 and 412. In this state, when the user observes an image, the right eye image and the left eye image do not suitably overlap with each other, and hence the image may be blurred or out-of-focus. Further, the image display areas of the display surfaces 411 and 412 deviate from the field of view of the eyes, which causes eyestrain, for example.

Meanwhile, the activated HMD 1 detects the tilt of the main body 4 with respect to the horizontal plane about the y-axis by the acceleration sensor 61 of the detector 6 (Step ST104). The detection may be continuously performed or may be intermittently performed at predetermined intervals. The acceleration sensor 61 outputs a signal relating the angle of the tilt, which is formed of a voltage or the like proportional to the acceleration, to the controller 72.

Next, the controller 72 calculates the angle of the tilt according to a signal from the acceleration sensor 61 (Step ST105). In addition, whether the head-mounted display is in the first state in which such an angle is equal to or larger than a predetermined angle or a second state in which such an angle is smaller than the predetermined angle (Step ST106).

When the controller 72 determines that the head-mounted display is in the second state (No in Step ST106), the LED 712 lights up (Step ST110). With this, it is estimated that the relative position is suitable, and the length of the band 52 is adjusted so that the relative position of the HMD 1 to the user is fixed (Step ST111). By adjusting the length of the band 52 to be shorter via the adjustment member 532 and sandwiching the head of the user by the forehead pad 55 and the band 52 in the front and rear directions, the relative position of the main body 4 to the user in the front and rear directions is defined.

Meanwhile, when the controller 72 determines that the head-mounted display is in the first state (Yes in Step ST106), the controller 72 further determines a direction of the tilt of the main body 4 with respect to the horizontal plane about the y-axis (Step ST107). When the direction of the tilt is the left tilt direction (Yes in Step ST107), the controller 72 causes the LED 713 to light up (Step ST108). Here, the left tilt direction indicates such a direction that the height on the display surface 411 side rotates downward. Meanwhile, when the direction of the tilt is the right tilt direction (No in Step ST107), the controller 72 causes the LED 711 to light up (Step ST110). For example, in the case shown in FIG. 8, it is determined that the direction of the tilt is the left tilt direction, the LED 713 lights up.

When the light of the LEDs 711 and 713 is seen, it is considered that the left and right directions of the main body 4 tilt with respect to the horizontal plane and the main body 4 is not located at the suitable relative position. Further, when the light of the LED 713 is seen, the main body 4 is tilted to the right-hand direction about the y-axis. Meanwhile, when the light of the LED 711 is seen, the main body 4 is tilted to the left-hand direction about the y-axis. In this manner, the relative position is re-adjusted (Step ST103). Further, at this time, if necessary, the length of the bands 51 and 52 is re-adjusted. In this manner, the HMD 1 repeats the above-mentioned operations until the LED 712 lights up (Steps ST103 to 107).

As described above, the HMD 1 according to this embodiment displays, with the light of the LEDs 711 to 713, whether or not the tilt of the main body 4 with respect to the horizontal plane about the y-axis falls within an acceptable range or which direction the main body 4 is tilted to if the main body 4 tilts departing from the acceptable range. With this, even the helper who has difficulties for grasping the position relationships between the eyes of the user and the display surfaces 411 and 412 can adjust the relative position of the HMD 1 to be the suitable relative position while checking the light of the LEDs 711 to 713.

Therefore, for example, even in the case where it is necessary to mount the HMD 1 during a surgery, the HMD 1 can be mounted at the suitable relative position without the user touching the HMD 1 by himself or herself. Further, with this, it becomes possible for the user to smoothly perform the endoscopic surgery while viewing comfortable 3D images.

Further, even in the case where the user cannot turn his or her face toward the helper, the LEDs 711 to 713 are arranged on the left side surface 411 of the main body 4, and hence the helper can easily acquire information on the angle of the tilt of the HMD 1 while being on the side of the user, so that the relative position can be adjusted.

In addition, by the mounting portion 5 having the above-mentioned configuration, the length of the bands 51 and 52 can be easily changed, and hence it becomes possible for the helper to easily perform the mounting, the adjustment and fixing of the relative position, and the like.

Second Embodiment

Figure 9:
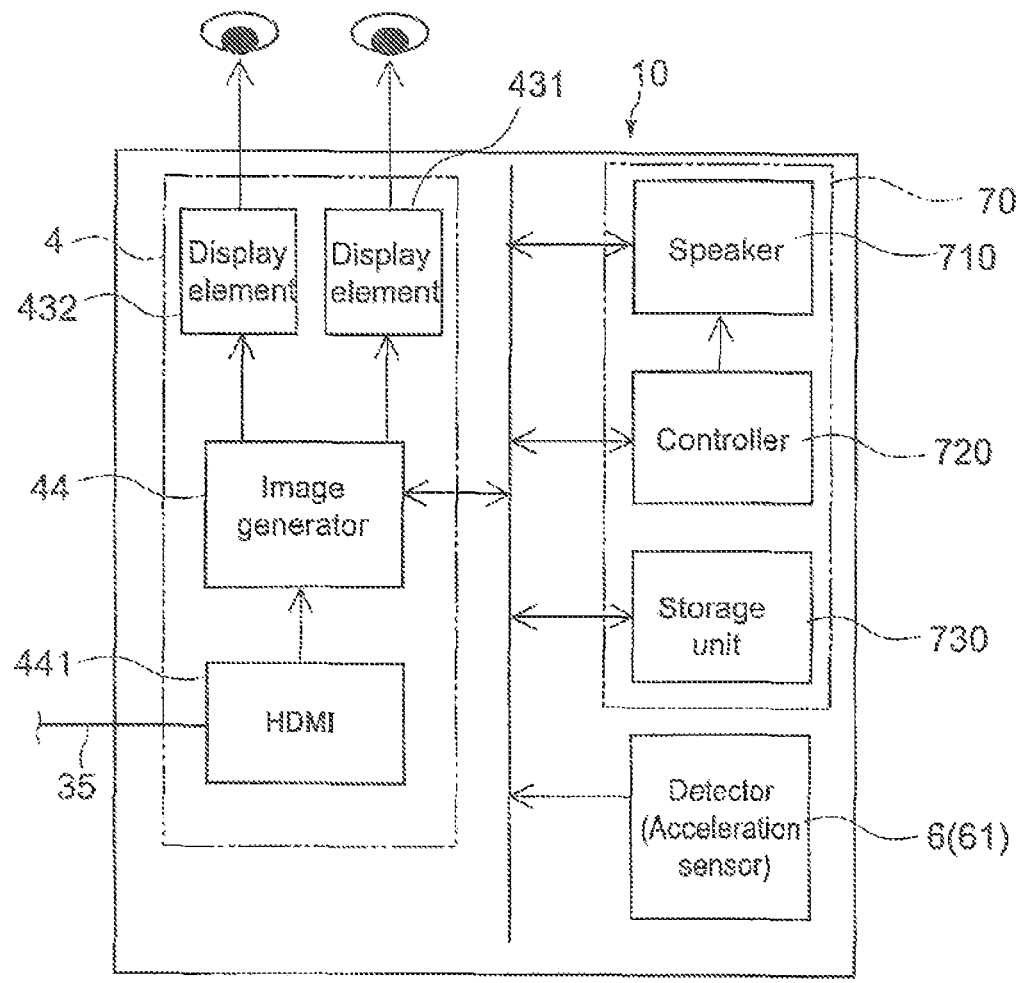
FIG. 9 is a block diagram showing an apparatus configuration of a head-mounted display according to a second embodiment of the present technology.

FIG. 9 is a block diagram showing an apparatus configuration of an HMD 10 according to a second embodiment of the present disclosure. This embodiment is different from the first embodiment mainly in that an output unit 70 includes a speaker 710 instead of the display unit. Note that, in the figure, parts corresponding to those of the first embodiment described above will be denoted by the same reference signs and detailed descriptions thereof will be omitted.

The output unit 70 according to this embodiment includes the speaker 710, a controller 720, and a storage unit 730. The speaker 710 is provided to the main body 4 of the HMD 10. The controller 720 and the storage unit 730 are housed in the casing 41, for example, as in the first embodiment.

Basic configuration of the controller 720 is the same as that of the controller 72 according to the first embodiment. That is, the controller 720 performs predetermined arithmetic processing according to a program stored in the storage unit 730 and makes a predetermined determination based on the processing result. In addition, the determination result is outputted to the speaker 710.

Specifically, the controller 720 calculates, according to a signal outputted from the acceleration sensor 61, the angle of the tilt of the main body 4 with respect to the horizontal plane about the y-axis. In addition, based on the calculation result, whether or not the head-mounted display is in the first state in which the angle of the tilt is equal to or larger than a predetermined angle or the second state in which the angle of the tilt is smaller than the predetermined angle is determined. The controller 720 according to this embodiment only outputs information on the first state to the speaker 710 without making a determination regarding the tilt direction.

The speaker 710 outputs the above-mentioned angle information regarding the tilt based on the determination of the controller 720. Specifically, a circuit is configured so that a buzzer sound is generated when the controller 720 determines that the head-mounted display is in is the first state. Meanwhile, the circuit is configured so that the buzzer sound is not generated when the controller 720 determines that the head-mounted display is in the second state.

Therefore, by checking the buzzer sound, the helper can estimate that the main body 4 of the HMD 10 tilts about the y-axis, and hence can adjust the relative position of the main body 4 to the user. Further, by continuing adjusting the main body 4 until the buzzer sound is no longer generated, the helper can adjust the main body 4 to be located at the suitable relative position.

In addition, the helper can receive a notification by the speaker 710 from any direction with respect to the HMD 10. Therefore, with the HMD 10 according to this embodiment, a degree of free of a standing position of the helper with respect to the user is increased, and it is easier for the helper to assist the mounting.

Note that, the configuration of the output unit 70 according to this embodiment is not limited to the above-mentioned configuration. For example, a configuration in which different buzzer sounds are generated depending on the first state and the second state may be used. Further, for example, as in the first embodiment, the controller 720 may be configured to further determine the direction of the tilt with respect to the horizontal plane when determining that the head-mounted display is in the first state. In this case, the speaker 710 may be configured to generate different kinds of buzzer sounds depending on the tilt direction.

Further, audio generated from the speaker 710 is not limited to the buzzer sound and may be an announcement sound or the like indicating the determination result of the controller 720.

Third Embodiment

Figure 10:
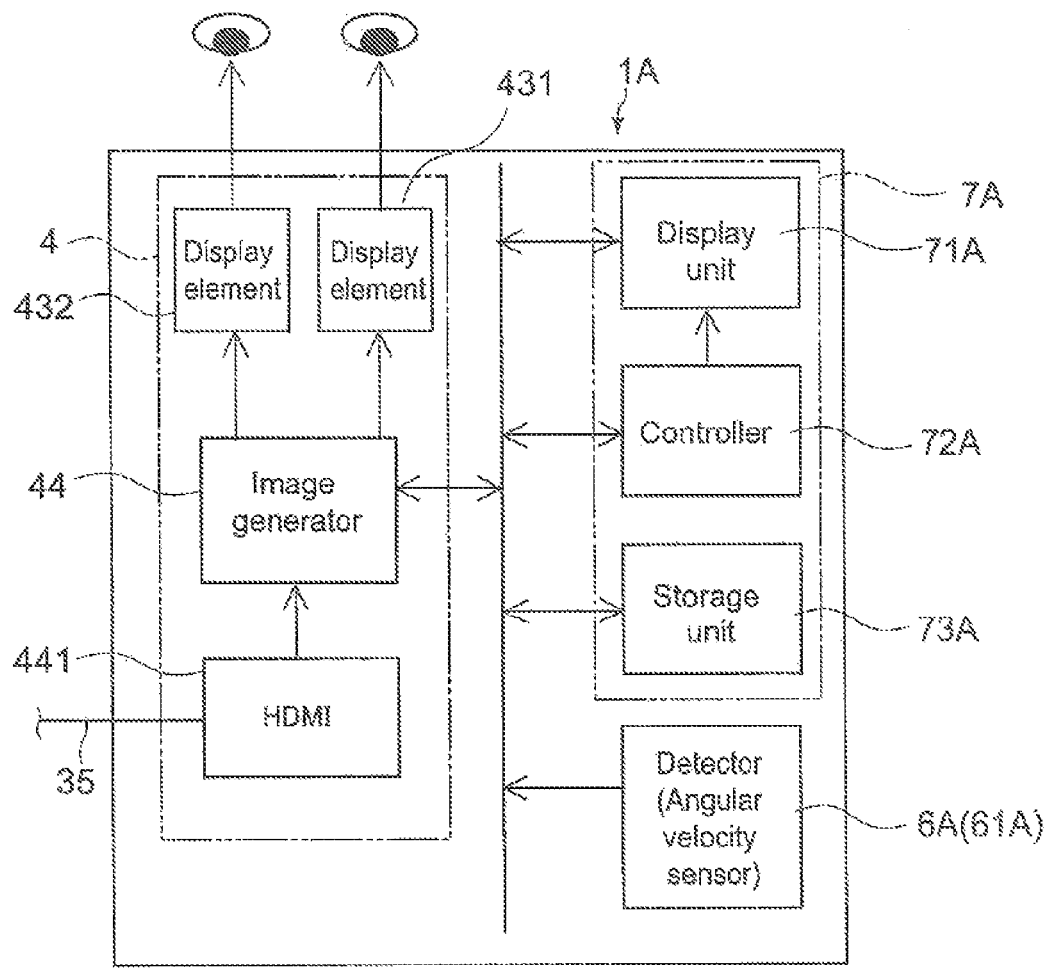
FIG. 10 is a block diagram showing an apparatus configuration of a head-mounted display according to a third embodiment of the present technology.

FIG. 10 is a block diagram showing an apparatus configuration of an HMD 1A according to a third embodiment of the present disclosure. This embodiment is different from the first embodiment mainly in that a detector 6A includes an angular velocity sensor 61A instead of the acceleration sensor 61. Note that, in the figure, parts corresponding to those of the first embodiment described above will be denoted by the same reference signs and detailed descriptions thereof will be omitted.

The angular velocity sensor 61A is typically a gyro sensor and is provided to the main body 4 as in the first embodiment. The angular velocity sensor 61A outputs angular velocity involved due to the rotation of the main body 4 about the y-axis as an electrical signal, to thereby output a signal relating to the angle of the tilt to a controller 72A of an output unit 7A. Although, for example, a vibration type gyro sensor or the like is used as the angular velocity sensor 61A, the angular velocity sensor 61A is not particularly limited.

That is, the detector 6A according to this embodiment is configured to detect, for example, when the HMD 1A is mounted on the user and then the main body 4 gradually tilts with respect to the horizontal plane and the relative position thereof is changed, angular velocity due to the change of the angle of the tilt.

The output unit 7A includes a display unit 71A, the controller 72A, and a storage unit 73A. In this embodiment, the configuration of the display unit 71A is the same as that of the first embodiment, but an arithmetic method for the angle of the tilt by the controller 72A is different. That is, according to the signal relating to the angular velocity from the output unit 7A, the controller 72A integrates the angular velocity by a predetermined period of time, to thereby calculate the angle of the tilt in this period of time.

In addition, based on the calculated angle of the tilt, as in the first embodiment, the controller 72A determines whether the head-mounted display is in the first state or the second state, and, when the head-mounted display is in the first state, whether the tilt direction is the right tilt direction or the left tilt direction. With this, the display unit 71A notifies the helper of information regarding the tilt. The helper receiving such information can adjust the relative position of the main body 4 to the user according to the display of the display unit 71A.

Note that, a start point of the "predetermined period of time" may be set to be a point of time when the angular velocity sensor 61A is activated. Further, with the relative position of the main body 4 to the user at the start point being a reference, the angle of the tilt about the y-axis is calculated. The activation method for the angular velocity sensor 61A is not particularly limited. For example, a switch or the like for activating the angular velocity sensor 61A may be provided to the main body 4, the processor unit 3, or the like. Further, the angular velocity sensor 61A may be activated in synchronization with the activation of the HMD 1A.

As described above, with the HMD 1A according to this embodiment, even in the case where the main body 4 of the HMD 1A tilts about the y-axis and the relative position of the main body 4 to the user is changed after the mounting, it is possible to detect an angle of the tilt and notify the helper of information regarding the angle. With this, in the case where the relative position of the HMD 1 is changed in use of the endoscope apparatus 2, the position can be adjusted.

Although the embodiments of the present technology are described above, the present technology is not limited thereto and various modifications can be made based on the technical concept of the present technology.

For example, although, in the first embodiment, the acceleration sensor 61 of the detector 6 outputs the signal relating the angle of the tilt with respect to the horizontal plane about the y-axis, the following modified example may also be employed. That is, the acceleration sensor 61 may be configured to be capable of outputting the signal relating to the angle of the tilt with respect to the horizontal plane about the x-axis. With this, in the case where the helper mounts the HMD 1 on the user in the front, it is possible to detect a tilt of the main body 4 in the front and rear directions, which would be otherwise particularly difficult to grasp.

In the case of the modified example above, the acceleration sensor 61 may be formed of, for example, the two-axis acceleration sensor that outputs the electrical signals corresponding to the acceleration of gravity in the y-axis direction and the z-axis direction. Further, the single-axis acceleration sensor that outputs the signal corresponding to the acceleration of gravity in either one of the y-axis direction and the z-axis direction may be used.

Further, in the modified example above, the display unit 71 of the output unit 7 may be provided to the front surface 413. With this, in the case where the helper mounts the HMD 1 on the user in the front, it is easier for the helper to check the display unit 71.

Note that, the modified example above is applicable also to the second and third embodiments. That is, in the case where the modified example above is applied to the second embodiment, it is possible to output the angle information regarding the tilt of the main body 4 about the x-axis, which is detected by the acceleration sensor 61, by means of audio such as a buzzer. Meanwhile, in the case where the modified example above is applied to the third embodiment, even if the main body 4 of the HMD 1A tilts about the x-axis and the relative position of the main body 4 to the user is changed after the mounting, it is possible to detect an angle of the tilt and notify the helper of information regarding the angle.

Although, in the above-mentioned embodiments, the acceleration sensor or the angular velocity sensor may be used as the inertial sensor used for the detector, the inertial sensor is not limited thereto. For example, a geomagnetic sensor or the like may be used. Also with this, by detecting an orientation of geomagnetism, it is possible to detect the tilt of the main body.

Further, as the detector, the acceleration sensor and the angular velocity sensor may be provided. With this, both of adjustment of the relative position upon the mounting and adjustment after the mounting become possible. In addition, for example, an integral error of the angle of the tilt that is calculated based on the output of the angular velocity sensor can be corrected based on the output of the acceleration sensor. With this configuration, higher accurate detection becomes possible.

For example, in the first embodiment, the LEDs are used as the display unit, the display unit is not limited thereto. For example, as the display unit, a meter that displays the angle of the tilt of the main body about the y-axis may be used. The meter includes, for example, an indicator panel having scales indicating tilt angles and a pointer indicating a predetermined angle on the indicator panel, and can displays the angle of the tilt in an analog manner. With this, the determination processing in the controller becomes unnecessary and the magnitude of the angle of the tilt can be displayed in detail. Thus, it is easier to adjust the relative position.

Similarly, a digital display that displays the angle of the tilt of the main body with respect to the horizontal plane may be used as the display unit. Also with this configuration, the magnitude of the angle of the tilt can be displayed in detail.

As a modified example of the first embodiment, the display unit 7 may include a single LED or two LEDs. In the case where the display unit 7 includes the single LED, for example, the single LED may be configured to emit light only when it is determined that the head-mounted display is in the first state. In the case where the display unit 7 includes the two LEDs, for example, one LED may light up when it is determined that the head-mounted display is in the first state and the other LED may light up when it is determined that the head-mounted display is in the second state. Alternatively, in the case where the display unit 7 includes the two LEDs, the LEDs may each light up depending on the tilt direction when the head-mounted display is in the first state. With this configuration, it is possible to make the apparatus configuration simpler, which can achieve a reduction in weight and cost of the entire HMD.

Alternatively, the display unit 7 may include four or more LEDs. With this, it is possible to display the information regarding the angle of the tilt in more detail.

Alternatively, the determination result may be displayed by blinking of the LED of the display unit 7. Otherwise, the determination result may also be displayed by changing a period of time when the LED of the display unit 7 is lighting up, for example.

Further, according to operation instructions by the user or the like, the image generator of the main body may be configured to perform adjustment of the virtual image position, color, contrast, luminance, and the like, correction of various types of distortion of the above-mentioned optical system, color drift correction, etc. at the same time as the generation of the image signals.

It should be noted that the present technology may also be configured as follows.

(1) A head-mounted display, including a detector for detecting an angle of tilt of the head-mounted display; and an output unit for outputting an indication of the angle of tilt.

(2) The head-mounted display according to (1), wherein the detector includes an acceleration sensor.
(3) The head-mounted display according to (2), wherein the acceleration sensor includes a two-axis sensor.
(4) The head-mounted display according to (2), wherein the acceleration sensor includes a three-axis sensor.
(5) The head-mounted display according to (1), wherein the detector includes an angular velocity sensor.
(6) The head-mounted display according to (5), wherein the detector includes a gyroscope.
(7) The head-mounted display according to (1), wherein the output unit includes a display unit.
(8) The head-mounted display according to (7), wherein the display unit is operable to indicate one of tilt in a first direction and tilt in a second direction.
(9) The head-mounted display according to (7), wherein the display is operable to indicate whether or not the angle of tilt is less than a predetermined angle.
(10) The head-mounted display according to (7), wherein the display unit includes one or more light emitting diodes.
(11) The head-mounted display according to (10), further including a casing having a left side surface and a right side surface, and wherein the light emitting diodes are positioned on one of the left side surface and the right side surface.
(12) The head-mounted display according to (10), further including a casing having a front surface and an eye-side surface, and wherein the light emitting diodes are positioned on the front surface.
(13) The head-mounted display according to (7), wherein the display unit includes one or more light emitting diodes, at least one of the light emitting diodes illuminating to indicate an angle of tilt in a first direction, and at least one other of the light emitting diodes illuminating to indicate an angle of tilt in a second direction.
(14) The head-mounted display according to (7), wherein the display unit includes one or more light emitting diodes, the light emitting diodes emitting respective colors of light, a first color indicating that there is an angle of tilt in a first direction or a second direction, and a second color indicating that the angle of tilt is zero or substantially zero.
(15) The head-mounted display according to (14), wherein the second color is green.
(16) The head-mounted display according to (1), wherein the output unit includes a speaker.
(17) The head-mounted display according to (16), wherein a sound is generated when the angle of tilt is equal to or greater than a predetermined angle.
(18) A medical system, including a head-mounted display, wherein the head-mounted display includes a detector for detecting an angle of tilt of the head-mounted display; and an output unit for outputting an indication of the angle of tilt.
(19) The medical system according to (18), wherein the output unit includes a display unit.
(20) The medical system according to (19), wherein the display unit is operable to indicate whether or not the angle of tilt is less than a predetermined angle.
(21) The medical system according to (18), further including an endoscope apparatus operable to capture three-dimensional image data.
(22) The medical system according to (18), further including a processing unit coupled to the head-mounted display through a high definition multimedia interface.
(23) A method for adjusting a head-mounted display, including detecting an angle of tilt of the head-mounted display; and outputting an indication of the angle of tilt.
(24) A head-mounted display, including:
a main body including a first display surface for a left eye, and
a second display surface for a right eye, the first display surface and the second display surface being arranged along a first axis direction;
a mounting portion that is provided to the main body to be mountable on a head of a user so that the first and second display surfaces and the left and right eyes of the user are opposed to each other in a second axis direction orthogonal to the first axis direction;
a detector that is provided to the main body to detect a tilt of the main body about at least either one of a first axis and a second axis orthogonal to the first axis and generate a signal relating to an angle of the tilt; and
an output unit that is provided to the main body to output angle information regarding the tilt according to the signal of the detector.
(25) The head-mounted display according to (24), in which the detector is configured to generate a signal relating to an angle of the tilt with respect to a horizontal plane.
(26) The head-mounted display according to (25), in which the output unit further includes a controller configured to determine, according to the signal of the detector, whether the head-mounted display is in a first state in which the angle of the tilt is equal to or larger than a predetermined angle or a second state in which the angle of the tilt is smaller than the predetermined angle, and is configured to output different angle information depending on the first state and the second state.
(27) The head-mounted display according to (26), in which the controller is configured to further determine, when the controller determines that the head-mounted display is in the first state, whether a direction of the tilt of the main body with respect to the horizontal plane about the second axis is a first direction or a second direction different from the first direction.
(28) The head-mounted display according to any one of (24) to (27), in which
the output unit includes a display unit configured to display the angle information.
(29) The head-mounted display according to (28), in which the main body further includes first and second side surfaces that are opposed to each other in the first axis direction, and
the display unit is provided to at least either one of the first and second side surfaces.
(30) The head-mounted display according to (26) or (27), in which
the output unit includes a speaker configured to output the angle information based on the determination of the controller.
(31) The head-mounted display according to any one of (24) to (30), in which the detector includes an inertial sensor.
(32) The head-mounted display according to any one of (24) to (30), in which
the mounting portion includes an adjuster for adjusting a relative position of the main body to the user.

REFERENCE SIGNS LIST 1, 10, 1A head-mounted display
4 main body
5 mounting portion
6, 6A detector
7, 70, 7A output unit
411 first side surface (left side surface)
412 second side surface (right side surface)
421 first display surface (display surface)
422 second display surface (display surface)
53 adjuster
71, 71A display unit
710 speaker
72, 720, 72A controller

The invention claimed is:
1. A head-mounted display, comprising:
a main body having a first display surface to display a left eye image to a left eye of a user wearing the head-mounted display and a second display surface to display a right eye image to a right eye of the user;
a detector configured to detect an angle of tilt of the head-mounted display relative to the left eye and the right eye of the user when the head-mounted display is worn by the user, the angle of tilt providing an indication as to whether the first display surface and the second display surface are respectively correctly aligned with the left eye and the right eye of the user; and
an output indicator for presenting a visible indication of the angle of tilt to a person other than the user wearing the head-mounted display or a sound indication of the angle of tilt.
2. The head-mounted display as recited in claim 1, wherein the detector comprises an acceleration sensor.
3. The head-mounted display as recited in claim 2, wherein the acceleration sensor comprises a two-axis sensor.
4. The head-mounted display as recited in claim 2, wherein the acceleration sensor comprises a three-axis sensor.
5. The head-mounted display as recited in claim 1, wherein the detector comprises an angular velocity sensor.
6. The head-mounted display as recited in claim 5, wherein the detector comprises a gyroscope.
7. The head-mounted display as recited in claim 1, wherein the output indicator comprises a display.
8. The head-mounted display as recited in claim 7, wherein the display is operable to indicate one of tilt in a first direction or tilt in a second direction.
9. The head-mounted display as recited in claim 7, wherein the display is operable to indicate whether or not the angle of tilt is less than a predetermined angle.
10. The head-mounted display as recited in claim 7, wherein the display comprises one or more light emitting diodes.
11. The head-mounted display as recited in claim 10, further comprising a casing having a left side surface and a right side surface, and wherein the light emitting diodes are positioned on one of the left side surface or the right side surface.
12. The head-mounted display as recited in claim 10, further comprising a casing having a front surface and an eye-side surface, and wherein the light emitting diodes are positioned on the front surface.
13. The head-mounted display as recited in claim 7, wherein the display comprises two or more light emitting diodes, at least one of the light emitting diodes illuminating to indicate an angle of tilt in a first direction, and at least one other of the light emitting diodes illuminating to indicate an angle of tilt in a second direction.
14. The head-mounted display as recited in claim 7, wherein the display comprises one or more light emitting diodes, the light emitting diodes emitting respective colors of light, a first color indicating that there is an angle of tilt in a first direction or a second direction, and a second color indicating that the angle of tilt is zero or substantially zero.

15. The head-mounted display as recited in claim 14, wherein the second color is green.

16. The head-mounted display as recited in claim 1, wherein the output indicator comprises a speaker.

17. The head-mounted display as recited in claim 16, wherein a sound is generated when the angle of tilt is equal to or greater than a predetermined angle.

18. A medical system, comprising:
- a head-mounted display, wherein the head-mounted display comprises (i) a main body having a first display surface to display a left eye image to a left eye of a user wearing the head-mounted display and a second display surface to display a right eye image to a right eye of the user, and (ii) a detector configured to detect an angle of tilt of the head-mounted display relative to the left eye and the right eye of the user when the head-mounted display is worn by the user, the angle of tilt providing an indication as to whether the first display surface and the second display surface are respectively correctly aligned with the left eye and the right eye of the user; and
- an output indicator for presenting a visible indication of the angle of tilt to a person other than the user wearing the head-mounted display or a sound indication of the angle of tilt.

19. The medical system as recited in claim 18, wherein the output indicator comprises a display.

20. A method for adjusting a head-mounted display having a main body with a first display surface to display a left eye image to a left eye of a user wearing the head-mounted display and a second display surface to display a right eye image to a right eye of the user, said method comprising:
- detecting, by use of a detector device, an angle of tilt of the head-mounted display relative to the left eye and the right eye of the user when the head-mounted display is worn by the user, the angle of tilt providing an indication as to whether the first display surface and the second display surface are respectively correctly aligned with the left eye and the right eye of the user; and
- presenting a visible indication of the angle of tilt to a person other than the user wearing the head-mounted display or a sound indication of the angle of tilt.

* * * * *